(12) United States Patent
Klein et al.

(10) Patent No.: US 7,898,657 B2
(45) Date of Patent: Mar. 1, 2011

(54) SYSTEM AND METHOD FOR VERIFYING THE CONTENTS OF A FILLED, CAPPED PHARMACEUTICAL PRESCRIPTION

(75) Inventors: Peter A. Klein, Durham, NC (US); Wang-Long Zhou, Andover, MA (US); Yongwu Yang, Bellmont, MA (US); Victor Sapirstein, Pound Ridge, NY (US); Jesse Samuel Eberdt, III, Durham, NC (US); W. L. Douglas Townsend, Jr., Durham, NC (US)

(73) Assignee: Parata Systems, L.L.C., Durham, NC (US)

( * ) Notice: Subject to any disclaimer, the term of this patent is extended or adjusted under 35 U.S.C. 154(b) by 335 days.

(21) Appl. No.: 11/972,849

(22) Filed: Jan. 11, 2008

(65) Prior Publication Data

US 2008/0183410 A1 Jul. 31, 2008

Related U.S. Application Data

(60) Provisional application No. 60/880,247, filed on Jan. 12, 2007.

(51) Int. Cl.
 *G01J 3/44* (2006.01)
(52) U.S. Cl. ..................................... 356/301
(58) Field of Classification Search ................. 356/301; 702/82; 359/871
See application file for complete search history.

(56) References Cited

U.S. PATENT DOCUMENTS

| | | | |
|---|---|---|---|
| 6,310,686 B1 | 10/2001 | Jiang | |
| 6,373,567 B1 | 4/2002 | Wise et al. | |
| 6,667,808 B2 * | 12/2003 | Clermont et al. | ............. 356/451 |
| 6,771,369 B2 | 8/2004 | Rzasa et al. | |
| 6,847,899 B2 * | 1/2005 | Allgeyer | ....................... 702/32 |

(Continued)

FOREIGN PATENT DOCUMENTS

WO    WO 97/48329    12/1997

(Continued)

OTHER PUBLICATIONS

International Search Report and Written Opinion of the International Searching Authority for PCT/US2008/000387 mailed Jun. 25, 2008.

*Primary Examiner*—Tarifur Chowdhury
*Assistant Examiner*—Abdullahi Nur
(74) *Attorney, Agent, or Firm*—Myers Bigel Sibley & Sajovec (57) ABSTRACT

A probe for a system for determining the chemical signature of a pharmaceutical compound. The probe comprises: a housing; an inlet in the housing adapted to be connected to a transmitting optical fiber; a scanning aperture in the housing; a receiving outlet in the housing adapted to be connected to a receiving optical fiber; at least one transmission reflector positioned in the housing to receive laser light from the transmitting optical fiber and reflect the laser light through the detection outlet to a pharmaceutical vial containing a pharmaceutical compound positioned outside the housing, and at least one receiving reflector positioned in the housing to receive light reflected by the pharmaceutical compound and reflect the light to the receiving outlet. This configuration can enable rapid and accurate scanning of a pharmaceutical contained in a vial positioned adjacent the detection outlet.

25 Claims, 4 Drawing Sheets

U.S. PATENT DOCUMENTS

2004/0046121 A1* 3/2004 Golden et al. .......... 250/339.07
2004/0263843 A1 12/2004 Knopp et al.
2005/0248759 A1 11/2005 Wang et al.
2007/0008523 A1 1/2007 Kaye et al.

FOREIGN PATENT DOCUMENTS

WO  WO 2006/036434 A2  4/2006

* cited by examiner

SYSTEM AND METHOD FOR VERIFYING THE CONTENTS OF A FILLED, CAPPED PHARMACEUTICAL PRESCRIPTION

RELATED APPLICATION

This application claims priority from U.S. Provisional Patent Application Ser. No. 60/880,247, filed Jan. 12, 2007, the disclosure of which is hereby incorporated herein in its entirety.

FIELD OF THE INVENTION

The present invention is directed generally to the identification of pharmaceuticals, and more particularly to the automatic identification of dispensed pharmaceuticals.

BACKGROUND OF THE INVENTION

There is an ongoing and predicted long-term shortage of licensed pharmacists. Due to the increasing age of the population and the ever-increasing number of prescription medicines available, the demand for prescription drugs is growing at rate that will far exceed the capacity and numbers of licensed pharmacists. The net impact of this imbalance is that pharmacists are increasingly spending more time doing clerical and administrative tasks such as verifying filled prescriptions and checking data entry done by pharmacy technicians. Since the capacity of any one pharmacist is fixed, the output of a pharmacy has become constrained. Consequently, the labor and total cost per prescription continues to rise. The December 2000 Department of Health and Human Services Report to Congress titled "The Pharmacist Workforce: A Study of the Supply and Demand for Pharmacists", which is hereby incorporated by reference into the present application, provides an overview of the above problem.

Due to these increased demands on a pharmacist's time, and the resulting increased reliance on technicians and other non-professional staff to fill prescriptions, there is an increased chance for prescription error. While these errors may take many forms, the likelihood of a dangerous or life threatening "adverse drug event" increases proportionally with the increased chance of prescription fill error. Several studies have shown that prescription error rates are consistently in the 2% to 7% range, with a 4% error rate often cited as a reliable average. The number of deaths due to medication errors is estimated to exceed 7,000 per year in the United States alone. Of course, this number does not include non-fatal conditions from drugs that also result in some form of trauma or injury. The resulting litigation costs associated with these prescription fill errors have also dramatically increased.

Many existing pharmacy filling systems and procedures still require a human operator, whether that operator is a technician or a licensed pharmacist, to validate visually whether the drug that is delivered to the customer is correct. Thus, the human factor can contribute to the majority of prescription fill errors. Existing visual verification techniques rely on comparing an electronic image of the prescribed medication, i.e., a picture of the prescribed medication retrieved from a data library, with the actual medication that is dispensed for the patient. Other systems and procedures rely on comparing the dispensed medication with that in the original manufacturer's supply container, or comparing an electronic image of the filled prescription with an electronic image of the prescribed medication retrieved from a data library.

Each of these verification systems present similar problems. First, these known verification methods assume that all drugs are visually distinct. This assumption causes many problems because many drugs are not, in fact, visually distinct and, in other cases, the visual differences between drugs is very subtle. For instance, manufacturers are rapidly running out of unique shapes, colors and sizes for their solid dosage form products. To further complicate the problem, generic drug manufactures may be using shapes, colors, and sizes that are different than that of the original manufacturer. Second, even though some known systems may utilize a National Drug Code (NDC) bar code to verify that the supply bottle being accessed corresponds correctly to the patient's prescription, a fraction of filled prescriptions that are never picked up are returned to the supply shelves for reuse in later prescriptions. These reused bottles will not, therefore, have a manufacturer's bar code on them. It is, therefore, difficult, if not impossible, to incorporate such validation schemes for these unused prescriptions. Furthermore, in these circumstances, a supply bottle is not available for a visual comparison with the filled prescription. Finally, each of these known manual verification and validation techniques typically requires that the pharmacist spend a significant portion of his day performing these administrative or clerical tasks and allows less time for patient consultation and other professional pharmacist activities.

Solid dosage pharmaceuticals (e.g. pills, tablets, and capsules) each have a unique chemical composition associated with them. This is often referred to as a chemical signature or fingerprint. Pharmaceuticals with varying dosage levels of the same active ingredient may have unique chemical signatures as well. Even slight variations in the active ingredient typically produce a unique chemical signature. In that regard, most pharmaceuticals can be identified accurately by the use of some form of chemical analysis. This same methodology may be applied to other forms of medication (e.g. liquids, creams, and powders). Particularly with solid dosage pharmaceutical products, while a group or package of products may look identical in the visible portion of the spectrum each product may have a unique chemical signature in the near-infrared wavelength range (800 to 2500 nm). For example, U.S. Pat. No. 6,771,369 to Rzasa et al. describes a pharmaceutical discrimination system that relies on NIR for scanning the contents of a pharmaceutical vial. As another example, U.S. Pat. No. 7,218,395 to Kaye et al. describes the use of Raman spectroscopy for scanning vial contents.

Each of these systems may have shortcomings related to the time spent scanning and/or the accuracy produced by the scan. As such, other techniques for automatically scanning a dispensed pharmaceutical may be desirable.

SUMMARY OF THE INVENTION

As a first aspect, embodiments of the present invention are directed to a probe for a system for determining the chemical signature of a pharmaceutical compound. The probe comprises: a housing; an inlet in the housing adapted to be connected to a transmitting optical fiber; a scanning aperture in the housing; a receiving outlet in the housing adapted to be connected to a receiving optical fiber; at least one transmission reflector positioned in the housing to receive laser light from the transmitting optical fiber and reflect the laser light through the detection outlet to a pharmaceutical vial containing a pharmaceutical compound positioned outside the housing, and at least one receiving reflector positioned in the housing to receive light reflected by the pharmaceutical compound and reflect the light to the receiving outlet. This configuration can enable rapid and accurate scanning of a pharmaceutical contained in a vial positioned adjacent the detection outlet.

As a second aspect, embodiments of the present invention are directed to a system for determining the chemical signature of a pharmaceutical compound in a vial, comprising: a stage configured to receive and hold a pharmaceutical vial; a spectrometer; a fiber optic bundle connected to the spectrometer, the fiber optic bundle including a transmitting optical fiber and a receiving optical fiber; and a probe. The probe comprises: a housing; an inlet in the housing connected to the transmitting optical fiber; a detection outlet in the housing, the detection outlet positioned adjacent the stage; a receiving outlet in the housing connected to the receiving optical fiber; at least one transmission reflector positioned in the housing to receive laser light from the transmitting optical fiber and reflect the laser light through the detection outlet to a pharmaceutical compound in a pharmaceutical vial positioned on the stage; and at least one receiving reflector positioned in the housing to receive light reflected by the pharmaceutical compound and reflect the light to the receiving optical fiber. The system further comprises a processor for processing optical signals from the pharmaceutical compound and comparing the processed signals with a database of known pharmaceutical compounds.

As a third aspect, embodiments of the present invention are directed to a method of verifying pharmaceuticals contained in a pharmaceutical vial. The method comprises: positioning a pharmaceutical vial containing a pharmaceutical adjacent a verification system; passing laser light along a transmission path from a laser generator to the pharmaceutical in the vial, the transmission path including at least one redirection of the laser light with a reflector; passing light reflected by the pharmaceutical along a receiving path from the pharmaceutical to a detector, the receiving path including at least one redirection of the light with a reflector; determining the chemical signature of the pharmaceutical based on the reflected light, determining the prescribed pharmaceutical for the vial based on a label affixed to the vial; and comparing the determined chemical signature against a database of known chemical signatures to determine whether the pharmaceutical contained in the vial is the pharmaceutical prescribed for the vial.

DETAILED DESCRIPTION OF EMBODIMENTS OF THE INVENTION

The present invention will now be described more fully hereinafter, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art. In the drawings, like numbers refer to like elements throughout. Thicknesses and dimensions of some components may be exaggerated for clarity.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein the expression "and/or" includes any and all combinations of one or more of the associated listed items.

In addition, spatially relative terms, such as "under", "below", "lower", "over", "upper," "front," "rear" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly.

Well-known functions or constructions may not be described in detail for brevity and/or clarity.

Figure 1:
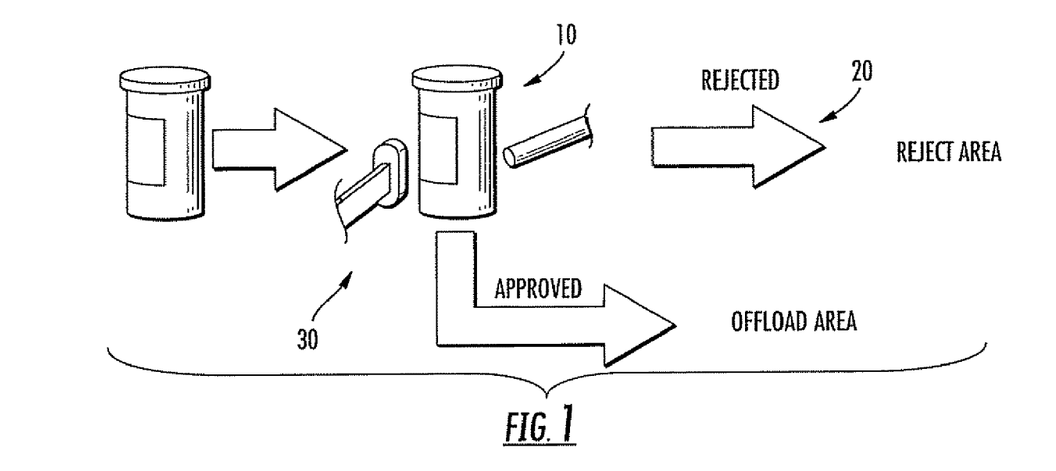
FIG. 1 is a schematic flow chart showing the process of verifying the contents of a filled pharmaceutical vial within an automated pharmaceutical vial filling system.
Figure 2:
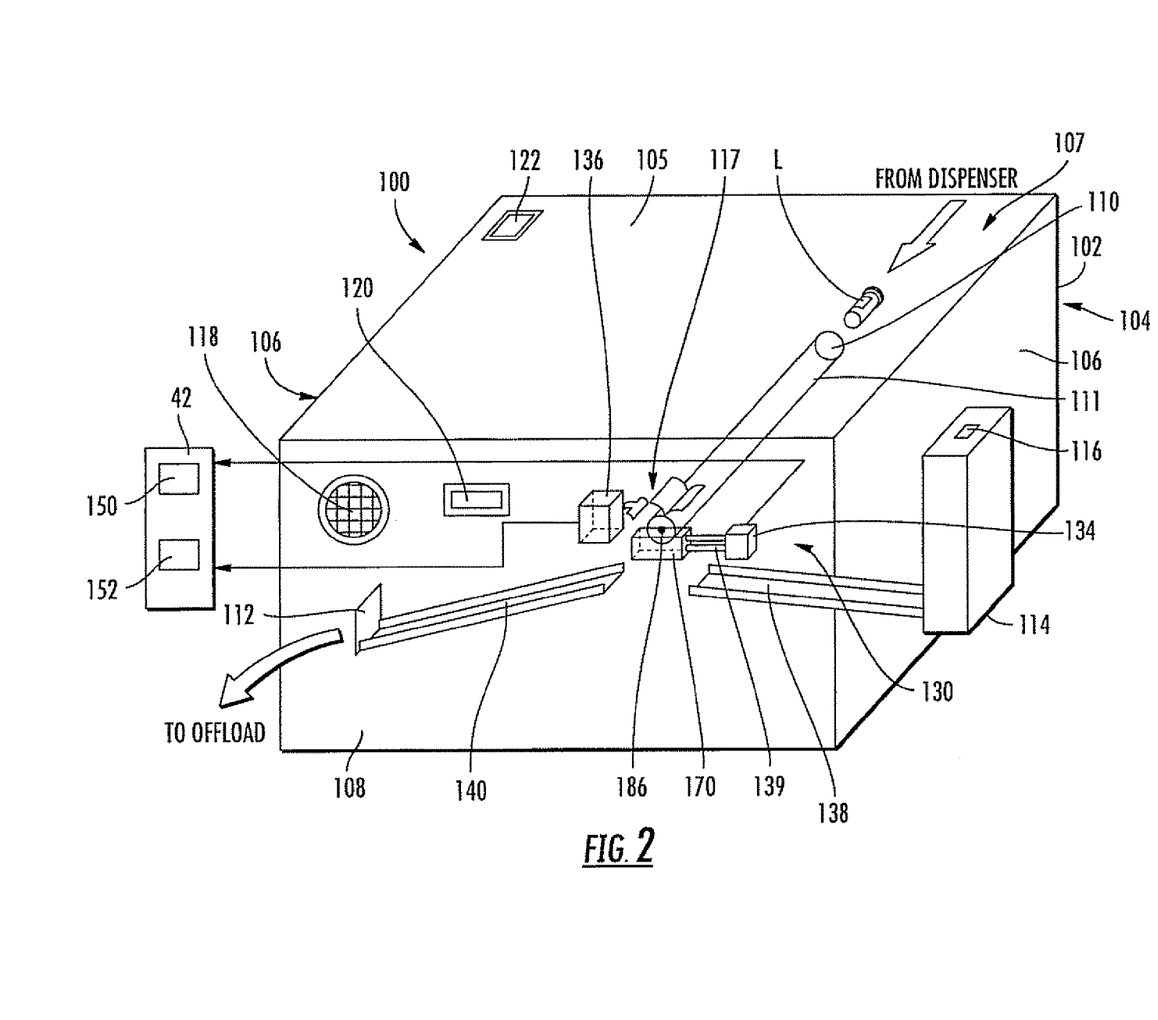
FIG. 2 is a schematic perspective view of a system for verifying the contents of a filled pharmaceutical vial.

Referring now to the figures, a filled vial verification station is illustrated in FIG. 2 and is designated broadly at 100. The verification station 100 is intended to verify that the contents of the vial are indeed the contents that the prescription calls for. Referring to FIG. 1, the basic operation of the station 100 begins with the sensing of the contents of the filled, labeled, capped vial through the vial (Step 10). If the contents of the vial match those that the system expects, the vial is accepted and conveyed to an offload station (Step 30). If instead the contents of the vial do not match those that the system expects, the vial is rejected and conveyed to a reject area (Step 20).

Turning now to FIG. 2, the verification station 100 includes a box-type housing 102 with a rear wall 104, a pair of side walls 106, a front wall 108 and a ceiling 105 that define a cavity 107. An entry opening 110 is present in the rear wall 104, from which a conveying tube 111 leads to a detection unit 130 (described in detail below). An exit opening 112 is present in one of the side walls 106.

Referring again to FIG. 2, a reject bin 114 is mounted to one of the side walls 106 and includes an opening (not shown)

for access to the cavity of the housing 102. The reject bin 114 illustratively includes a reject ID detector 116 (such as a biometric identifier) that limits external access to the reject bin 114 to authorized personnel.

Referring still to FIG. 2, the housing 102 may also include other optional components that can facilitate operation. A speaker 118 is mounted on the housing 102 to provide an audible signal regarding operations of the validation station 100. A display 122 is also mounted on the housing 102 to show the status of operations of the validation station 100, the identity of the prescription being processed, or the like. An external bar code reader 120 is also mounted on the housing 102 to enable an operator to manually scan the bar code on a filled, labeled pre-packaged or unit of use pharmaceutical if desired (for example, pre-packaged tablets in a patient compliance pack or a packet of birth control pills). Such a scan can facilitate the verification that the NDC on the package matches the pharmaceutical on the prescription order. All of these components are optional and may be omitted in some embodiments.

Referring again to FIG. 2, a detection unit 130 is positioned within the cavity 107 of the housing 102. The detection unit 130 includes a Raman spectrometer 134. The spectrometer 134 is positioned within the cavity 107 to enable the spectrometer 134 to scan the contents of a filled, labeled vial. The spectrometer 134 is connected electrically to a controller 42, which includes a memory module (not illustrated) for storing a spectral signature of a detected pharmaceutical compound. The spectrometer 134 also includes a probe 170 that is positioned adjacent a detection section 117 at the lower end of the conveying tube 111. The probe 170 is connected to the Raman spectrometer 134 via a transmitting fiber 137 of a fiber optic bundle 139. An exemplary fiber optic bundle is described in PCT Publication No. WO 07/019,460, the disclosure of which is hereby incorporated herein in its entirety.

Figure 3:
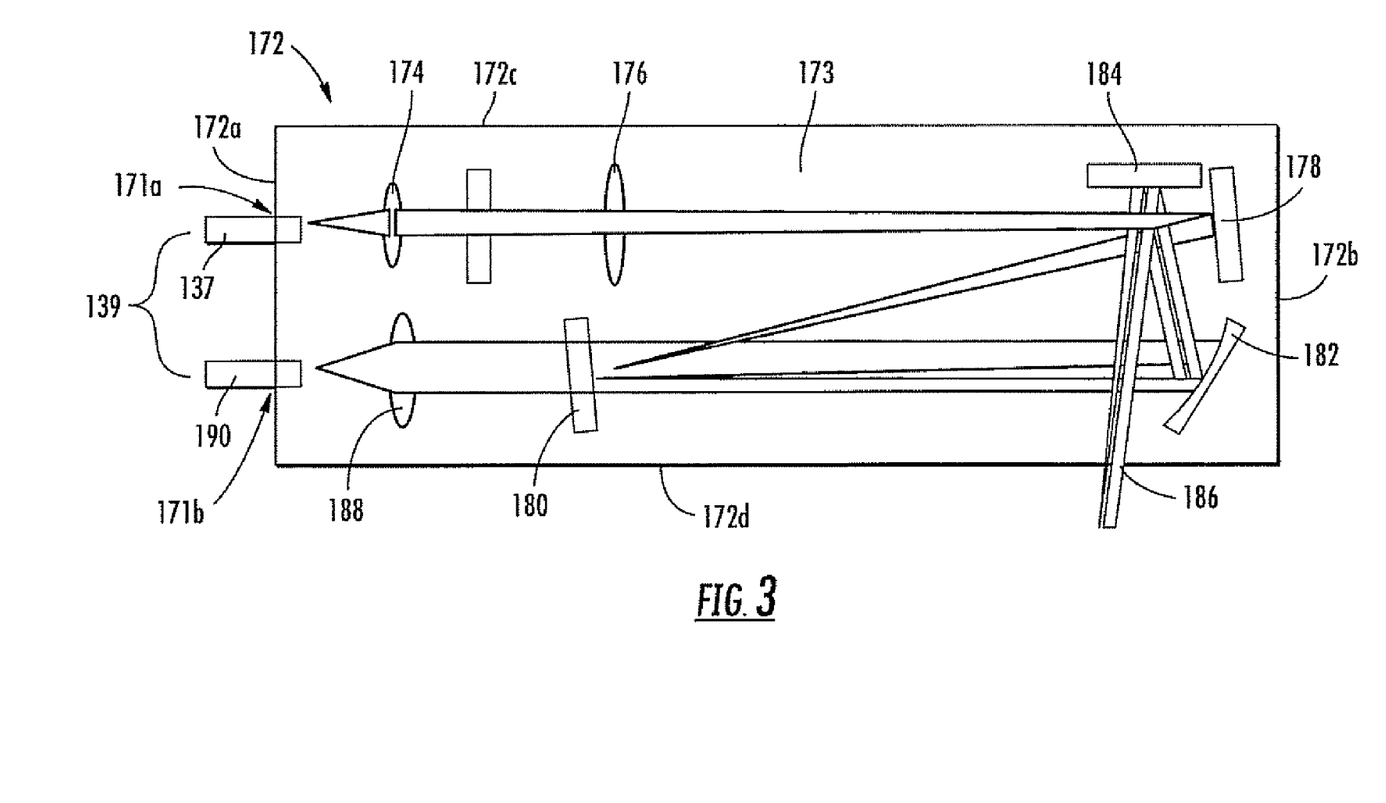
FIG. 3 is a section view of the probe of the Raman spectrometer of the system of FIG. 2.

Referring now to FIG. 3, the probe 170 includes a light-tight rectangular housing 172 that encloses a cavity 173. Within the cavity are components that focus, redirect, and otherwise manipulate light provided by the transmitting fiber 137 of the fiber bundle 139. In the illustrated embodiment, the transmitting fiber 137 presents light (in the form of a 0.2 mm laser) to the cavity 173 through an inlet 171a in one side wall 172a of the housing 172; the light then follows a transmission path through a plurality of reflectors (typically mirrors) to a scanning aperture 186 that is adjacent the detecting section 117 of the conveying tube 111. More specifically, the light (laser beam) passes from the transmitting fiber 137 first through a lens 174 that focuses the light, then through a laser-line filter that filters out noise spectrum of the light source and fiber, then through an adjacent lens 176 that further focuses the light. The light then passes to a reflector 178 mounted on the opposite side wall 172b of the housing 172. The reflector 178 is mounted at an oblique angle to the path of the entering light (in this instance, the angle is 6.5 degrees), such that the light is redirected at an angle of 13 degrees back toward the side wall 172a until it reaches another reflector 180. In the illustrated embodiment, the reflector 180 is mounted at a similar oblique angle to the reflector 178, such that the light exiting the reflector 180 travels on a path that is substantially parallel to the segment of the path between the lens 176 and the reflector 178. Light then passes to a concave reflector 182 that is mounted adjacent the side wall 172b at an angle of 40 degrees to the light path. The reflector 182 collimates or slightly focuses the laser light and redirects the light toward a reflector 184 that is mounted on a wall 172c of the housing 172. Light then reflects from the reflector 184 through the scanning aperture 186 in a wall 172d (which is opposite the wall 172c). Once through the scanning aperture 186, the light can pass into a pharmaceutical vial held in the detecting section 117 of the tube 111 (see FIG. 4) and be employed to detect the identity of the contents of the vial (the vial typically being held such that the tablet being detected is positioned between about 0.1 and 0.4 inches from the wall 172d).

When entering the vial, in the illustrated embodiment the light beam has a diameter of between about 2.5 and 3.5 mm, typically about 3 mm, an intensity of between about 200 and 500 milliwatts, and a wavelength of less than about 140 $cm^{-1}$. A beam of this diameter can increase the depth of field of the spectrometer, which can improve the accuracy of the spectrum (because tablets in a vial are not always at the same depth, increased depth of field can improve the chance of the system finding a table to detect). Also, the light beam enters the flat bottom surface of the vial at an oblique angle to the vial (between about 75 and 85 degrees), which can decrease the degree of undesirable back reflection from the vial surface.

Signal light is reflected from the vial to the Raman spectrometer along a receiving path that begins at the vial and proceeds through the aperture 186 to the reflector 184 and the reflector 182, then to a lens 188 mounted near the side wall 172a. The reflector 182 transmits Raman signal and rejects source light. For further purifying Raman spectrum, another Raman edge filter may be placed between the reflector 182 and the lens 188. The lens 188 focuses the returning light and directs it to a receiving fiber 190 of the fiber optic bundle 139 via a receiving outlet 171b in the side wall 172a, through which the light passes to the Raman spectrometer for detection and processing. Generation of the spectrum by the spectrometer 134 once light is received in the receiving fiber 190 is well-known and need not be described in detail herein; for further detail, Raman spectrometry and its underlying theory is described generally at, e.g., http://www.lambdasolutions.com/RamanTechNote_English.pdf the disclosure of which is hereby incorporated herein in its entirety. In some embodiments, the generation of the spectrum (.i.e., the chemical signal) of the pharmaceutical can involve the combination of the chemical signals of the pharmaceutical and the material of the vial (which is typically amber-colored polypropylene, although polycarbonate and PET may be used for liquids). Also, because scanning is typically relatively rapid (on the order of 0.1 seconds), in some embodiments multiple scans may be performed and the results averaged to provide a composite spectrum.

Referring once again to FIG. 2, the detection unit 130 further includes a second bar code scanner 136 that is positioned adjacent the detection section 117 so that it can scan the bar code on the filled, labeled vial. The bar code scanner 136 is also connected electrically to the controller 42. The bar code on the filled, labeled vial indicates, or is linked to data indicating, inter alia, the pharmaceutical that is prescribed and, therefore, should be present in the vial.

Figures 4, 5:
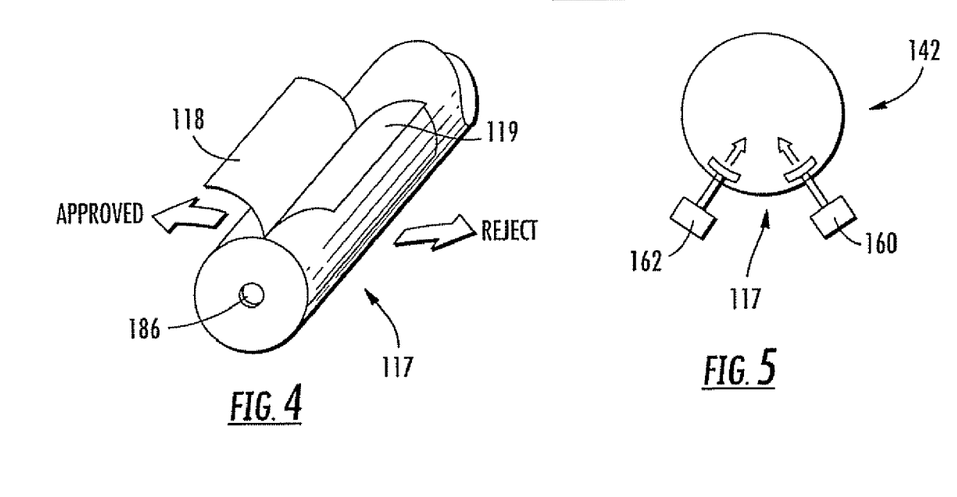
FIG. 4 is an enlarged partial perspective view of the detecting section of the conveying tube of the system of FIG. 2.
FIG. 5 is an enlarged end view of the detecting section of FIG. 2 with the doors shown in an open position.

Referring now to FIGS. 2, 4 and 5, a diverting unit 142 associated with the detecting section 117 is configured to receive a signal from the controller 42 and divert a filled, labeled vial to either an approved vial conveyer 140 or a rejected vial conveyor 138 based on the signal. The diverting unit 142 includes two plungers 160, 162, each of which is positioned below the detecting section 117 of the conveying tube 111. Two doors 118, 119 that are positioned on the upper portion of the detecting section 117 opposite the plungers 160, 162. Each of the doors 118, 119 is attached to the detecting section via a hinge that enables the door to pivot between a closed position, in which it covers the detecting section 117, and an open position, in which the detecting section 117 is open.

Referring still to FIG. 2, an approved vial conveyor 140 leads from the detection section 117 to the exit opening 112 in the side wall 106. A rejected vial conveyor 138 leads from the detecting section 117 to the opening in the reject bin 114.

In some embodiments, the verification station 100 also includes a stamping device (not shown). The stamping device is positioned outside the housing 102 at the end of the approved vial conveyor 140 and is electrically connected to the controller 42. In certain embodiments, the stamping device includes a proprietary ink cartridge that participates in the activation of the stamping device (such that the stamping device will not operate without the cartridge being in place).

Referring again to FIG. 2, the controller 42 includes modules that are associated with the detection unit 130. More specifically, the controller 42 includes a data base 150 that stores the prescription number (hereinafter the "Rx number") associated with each prescription, and a National Drug Code (NDC) number that corresponds to a particular pharmaceutical compound. Also, the controller 42 includes a data base 152 of spectral signatures, each of which corresponds to a particular pharmaceutical compound.

Figure 6:
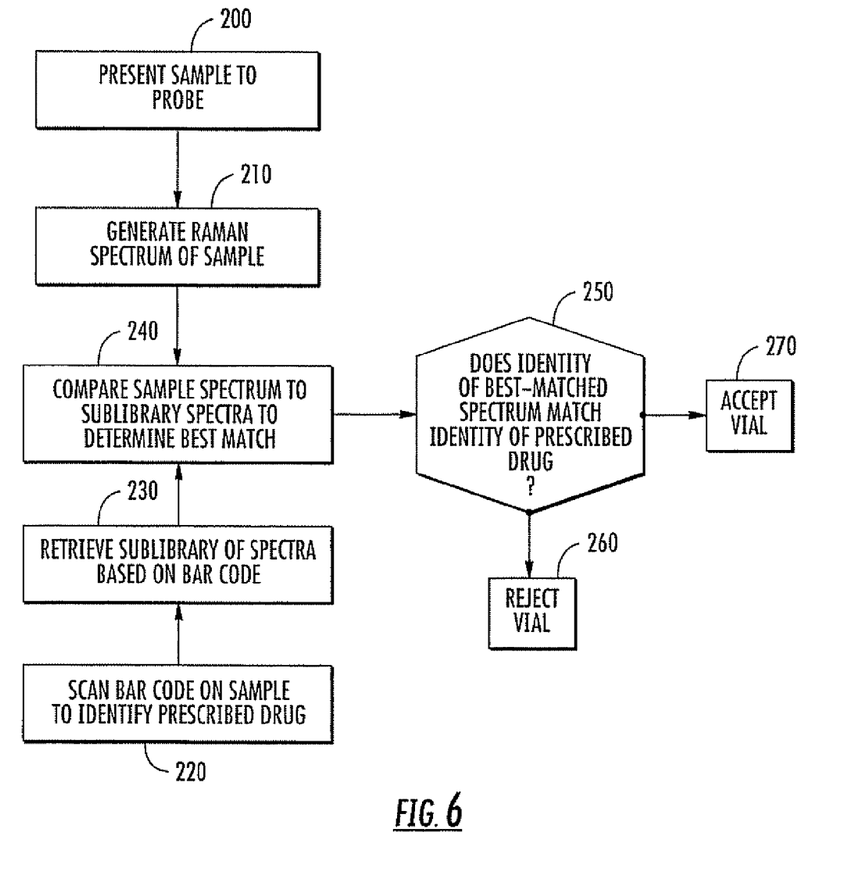
FIG. 6 is a flow chart representing the sequence of operations controlled by the controller of the system of FIG. 2.

In operation, and with reference to FIG. 6, a filled, labeled, capped vial V is deposited into the conveying tube 111 (this step can be performed manually by a pharmacist or automatically; for example, a robotic arm associated with an automated pharmaceutical dispensing machine such as that disclosed in U.S. Pat. No. 6,971,541 to Williams et al. may be employed). The conveying tube 111 conveys the vial V to the detecting section 117 (Step 200). When the vial V reaches the detecting section 117, the controller 42 (signaled by a proximity detector or the like that detects the presence of the vial V) signals the bar code scanner 136 to read the bar code on the label L of the vial V (Step 220). This information is passed to the controller 42, which identifies the Rx number and NDC number from the bar code.

Also, after the vial V arrives on the platform 132, the controller 42 signals the spectrometer 134 to scan the contents of the vial V through the vial floor via the probe 141. In some embodiments, the spectrometer 134 may also scan through the side of the vial (assuming favorable positioning and label orientation). In scanning the contents of the vial V, the spectrometer 134 generates a spectral signature of the compound in the vial V (Step 210).

Correlation of the scanned spectrum of the dispensed pharmaceutical and the identity of the prescribed pharmaceutical can be achieved in different ways. For example, as shown in FIG. 6, the bar code scanner 136 scans the bar code on the label L and, based on the identity of the prescribed pharmaceutical, retrieves a sublibrary of spectra from the database 150 (Step 230). As discussed above, separately the Raman spectrometer 134 generates a Raman spectrum for the compound in the vial via the probe 170. The controller 42 then compares the scanned spectral signature to the spectral signatures of the sublibrary to determine which spectrum is the best match for the scanned spectrum (Step 240). The identity of the best matched spectrum is then compared the identity of the prescribed pharmaceutical to determine whether they match (Step 250).

In alternative embodiments, the scanned spectrum can be compared directly to the spectrum of the prescribed pharmaceutical to determine whether they match. As another alternative, the scanned spectrum can be compared to all of the spectra in the database, the most closely matching spectrum can be identified, and the identity of that pharmaceutical can be compared to the identity of the prescribed pharmaceutical to determine whether they match.

If the identity of the prescribed pharmaceutical identified on the label of the vial V matches the identity of the pharmaceutical with the best matched spectrum, the vial V is deemed to contain the proper pharmaceutical compound, and the controller 42 actuates the diverting unit 142 to divert the vial V to the approved vial conveyor 140 by extending the plunger 160 and opening the door 118 (Step 270). This action propels the vial V to the approved vial conveyer 140, which then conveys the approved vial V to the stamping device. The stamping device stamps the vial V with a mark (often indelible) that indicates that the contents of the vial V have been validated. The vial V can then be conveyed, either manually or via another conveyor, to an offloading station.

If the identities of the pharmaceutical determined for the scanned vial V and the pharmaceutical identified by the NDC number on the vial V do not match, the controller 42 signals the diverting unit 142 to divert the vial V to the reject conveyor 138 by extending the plunger 162 and opening the door 119 (Step 260). This action propels the vial V into the reject conveyor 138, which conveys the vial V to the reject bin 114. The vial V remains in the reject bin 114 until it is removed by approved personnel who can open the reject bin 114 via the reject ID detector 116.

Those skilled in this art will appreciate that the systems and methods described above may vary. For example, either or both of the approved and rejected vials may be removed from the system manually, based on a visual or auditory signal. The probe may take a different configuration, with different numbers, locations and/or orientations of lenses, reflectors and the inlet and outlets. The configuration of the housing 102 may vary, as may the positions and orientations of the components contained therein. Other variations will be apparent to those of skill in this art.

The foregoing is illustrative of the present invention and is not to be construed as limiting thereof. Although exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined by the claims. The invention is defined by the following claims, with equivalents of the claims to be included therein.

That which is claimed is:

1. A probe for a system for determining the chemical signature of a pharmaceutical compound, comprising:
   a housing;
   an inlet in the housing adapted to be connected to a transmitting optical fiber;
   a scanning aperture in the housing;
   a receiving outlet in the housing adapted to be connected to a receiving optical fiber;
   at least one transmission reflector positioned in the housing to receive laser light from the transmitting optical fiber and reflect the laser light through the scanning aperture to a pharmaceutical vial containing a pharmaceutical compound positioned outside the housing, wherein the inlet, the at least one transmission reflector and the scanning aperture are configured and positioned such that the laser light has a diameter of between about 2.5 and 3.5 mm as it reaches the scanning aperture; and
   at least one receiving reflector positioned in the housing to receive light reflected by the pharmaceutical compound and reflect the light to the receiving outlet.

2. The probe defined in claim 1, wherein the housing includes side walls, and wherein the inlet is located in a first side wall and the scanning aperture is located in a second side wall.

3. The probe defined in claim 2, wherein the receiving outlet is located in the first side wall.

4. The probe defined in claim 2, wherein the second side wall is generally normal to the first side wall.

5. The probe defined in claim 1, wherein the at least one transmission reflector is a plurality of transmission reflectors.

6. The probe defined in claim 5, wherein one of the plurality of transmission reflectors is positioned to reflect laser light directly at the pharmaceutical vial at an angle of between about 75 and 85 degrees relative to a bottom surface of the pharmaceutical vial.

7. The probe defined in claim 5, wherein the plurality of transmission reflectors includes at least three transmission reflectors.

8. The probe defined in claim 5, wherein the plurality of transmission reflectors includes five transmission reflectors.

9. The probe defined in claim 1, further including a lens positioned to focus laser light transmitted between the inlet and the at least one reflector.

10. The probe defined in claim 1, wherein the at least one receiving reflector is a plurality of receiving reflectors.

11. The probe defined in claim 10, wherein one of the plurality of receiving reflectors positioned to receive light reflected from the pharmaceutical at an angle of between about 75 and 85 degrees relative to a bottom surface of the pharmaceutical vial.

12. The probe defined in claim 11, further comprising a lens located between one of the plurality of receiving reflectors and the receiving outlet, the lens configured to focus the reflected light as it passes through the receiving outlet.

13. The probe defined in claim 1, wherein the at least one transmission reflector is a plurality of transmission reflectors, and wherein the at least one receiving reflector is a plurality of receiving reflectors, and wherein at least one reflector serves as both a transmission reflector and a receiving reflector.

14. A system for determining the chemical signature of a pharmaceutical compound in a vial, comprising:
- a stage configured to receive and hold a pharmaceutical vial;
- a spectrometer;
- a fiber optic bundle connected to the spectrometer, the fiber optic bundle including a transmitting optical fiber and a receiving optical fiber; and
- a probe comprising:
  - a housing;
  - an inlet in the housing connected to the transmitting optical fiber;
  - a scanning aperture in the housing;
  - a detection outlet in the housing, the detection outlet positioned adjacent the stage;
  - a receiving outlet in the housing connected to the receiving optical fiber;
  - at least one transmission reflector positioned in the housing to receive laser light from the transmitting optical fiber and reflect the laser light through the scanning aperture to a pharmaceutical compound in a pharmaceutical vial positioned on the stage, wherein the inlet, the at least one transmission reflector and the scanning aperture are configured and positioned such that the laser light has a diameter of between about 2.5 and 3.5 mm as it reaches the scanning aperture; and
  - at least one receiving reflector positioned in the housing to receive light reflected by the pharmaceutical compound and reflect the light to the receiving optical fiber; and
- a processor for processing optical signals from the pharmaceutical compound and comparing the processed signals with at least one spectrum from a database of known pharmaceutical compounds.

15. The system defined in claim 14, further comprising a stamping device configured to indicate that a pharmaceutical vial has been approved.

16. The system defined in claim 14, further comprising structure for separating rejected vials from approved vials.

17. The system defined in claim 14, further comprising a bar code scanner positioned to scan a bar code on the pharmaceutical vial as it is positioned on the stage.

18. A method of verifying pharmaceuticals contained in a pharmaceutical vial, comprising:
- positioning a pharmaceutical vial containing a pharmaceutical adjacent a verification system;
- passing laser light along a transmission path from a laser generator through a scanning aperture to the pharmaceutical in the vial, the transmission path including at least one redirection of the laser light with a reflector, wherein the laser light has a diameter of between about 2.5 and 3.5 mm as it reaches the scanning aperture;
- passing light reflected by the pharmaceutical along a receiving path from the pharmaceutical to a detector, the receiving path including at least one redirection of the light with a reflector;
- determining the chemical signature of the pharmaceutical based on the reflected light;
- determining a prescribed pharmaceutical for the vial based on a label affixed to the vial; and
- comparing the determined chemical signature against a database of known chemical signatures to determine whether the pharmaceutical contained in the vial is the prescribed pharmaceutical for the vial.

19. The method defined in claim 18, wherein the step of determining the prescribed pharmaceutical for the vial comprises scanning indicia on the label affixed to the vial, the indicia indicating the prescribed pharmaceutical.

20. The method defined in claim 18, wherein the step of passing laser light comprises passing a beam of laser light that has a diameter of about 3.0 mm as the light reaches the vial.

21. The method defined in claim 18, further comprising the step of stamping the label affixed to the vial if the pharmaceutical in the vial matches the prescribed pharmaceutical.

22. The method defined in claim 18, wherein the vial has a flat bottom surface, and wherein the laser light is directed to the vial at an angle of between about 75 and 85 degrees relative to the vial bottom surface.

23. The method defined in claim 18, wherein the step of determining the chemical signature is performed with Raman spectroscopy.

24. The method defined in claim 18, wherein the wavelength of the laser light is less than about 140 $cm^{-1}$.

25. The method defined in claim 18, wherein an initial segment of the transmission path defines a first direction, and wherein an initial segment of the receiving path defines a second direction, and wherein the first and second directions are generally perpendicular.

* * * * *